(12) United States Patent
Monkhouse et al.

(10) Patent No.: US 6,280,771 B1
(45) Date of Patent: Aug. 28, 2001

(54) DOSAGE FORMS EXHIBITING MULTI-PHASIC RELEASE KINETICS AND METHODS OF MANUFACTURE THEREOF

(75) Inventors: Donald Monkhouse, Radnor; Jaedeok Yoo, Philadelphia, both of PA (US); Jill K. Sherwood, Princeton; Michael J. Cima, Princeton, both of NJ (US); Esteban Bornancini, Montgomery Township, PA (US)

(73) Assignees: Therics, Inc., Princeton, NJ (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/027,290

(22) Filed: Feb. 20, 1998

Related U.S. Application Data (60) Provisional application No. 60/037,741, filed on Feb. 20, 1997, provisional application No. 60/038,283, filed on Feb. 20, 1997, provisional application No. 60/039,109, filed on Feb. 26, 1997, provisional application No. 60/039,157, filed on Feb. 26, 1997, provisional application No. 60/039,110, filed on Feb. 26, 1997, provisional application No. 60/039,440, filed on Feb. 26, 1997, provisional application No. 60/041,048, filed on Mar. 21, 1997, provisional application No. 60/041,763, filed on Mar. 31, 1997, provisional application No. 60/042,154, filed on Mar. 31, 1997, and provisional application No. 60/051,042, filed on Jun. 27, 1997.

(51) Int. Cl.[7] .............................. A61K 9/20; A61K 9/26; A61K 9/48

(52) U.S. Cl. ................... 424/484; 424/422; 424/443; 424/451; 424/464; 424/465; 424/468; 424/469

(58) Field of Search .................................. 424/484, 485, 424/486, 487, 488, 422, 443, 451, 464, 465, 468, 469, 457

(56) References Cited

U.S. PATENT DOCUMENTS

| 4,131,648 | 12/1978 | Choi et al. | 424/22 |
| 5,204,055 | 4/1993 | Sachs et al. | 419/2 |
| 5,490,962 | * | 2/1996 | Cima et al. | 264/22 |
| 5,518,680 | 5/1996 | Cima et al. | 264/401 |

OTHER PUBLICATIONS

Sachs, et al., CAD–Casting: Direct Fabrication of Ceramic Shells and Cores by Three Dimensional Printing: *Manufacturing Review* 5(2), 117–126 (1992).

* cited by examiner

Primary Examiner—James M. Spear
(74) Attorney, Agent, or Firm—Seed IP Law Group PLLC (57) ABSTRACT

Dosage forms prepared by solid free form fabrication (SFF) provide release of medicament in multiple phases.

15 Claims, 2 Drawing Sheets

DOSAGE FORMS EXHIBITING MULTI-PHASIC RELEASE KINETICS AND METHODS OF MANUFACTURE THEREOF

This application claims benefit of U.S. Provisional Application No. 60/037,741 filed Feb. 20, 1997, No. 60/038,283 filed Feb. 20, 1997, No. 60/039,109 filed Feb. 26, 1997, No. 60/039,157 filed Feb. 26, 1997, No. 60/039,110 filed Feb. 26, 1997, No. 60/039,440 filed Feb. 26, 1997, No. 60/041,048 filed Mar. 21, 1997, No. 60/041,763 filed Mar. 31, 1997, 60/042,154 filed Mar. 31, 1997, and No. 60/051,042 filed Jun. 27, 1997 cited in the Declaration of the present application.

FIELD OF THE INVENTION

The invention relates to methods of controlled drug delivery. More specifically the invention relates to dosage forms incorporating one or more than one pharmaceutically active material.

BACKGROUND OF THE INVENTION

One of the problems with the current technology for drug delivery is the lack of precision and resulting lack of quality control. This in turn causes a lack of precision in the release rates of the encapsulated drug and requires that patients take the drug at specified times throughout the day. Oftentimes, especially for complex dosage regimes, patient compliance is well below acceptable levels, resulting in diminished therapeutic effect. Construction of drug delivery devices which could release drugs according to complex prescribed temporal patterns could have broad application for delivery of bioeffecting agents by both oral and implantable routes. For example, implants to areas of the body not easily accessed, such as the ocular cavity, can be designed for prolonged drug delivery. Dosage forms in which release of active coincides with circadian rythms are also possible. In addition, patient compliance problems can be obviated by reducing the number of times a patient must self administer drug.

U.S. Pat. No. 5,490,962 teaches the preparation of dosage forms using solid free-form fabrication (SFF) methods. These methods can be adapted for use with a variety of different materials to create dosage forms with defined compositions, strengths, and densities, through the use of computer aided design (CAD). Examples of SFF methods include stereo-lithography (SLA), selective laser sintering (SLS), ballistic particle manufacturing (BPM), fusion deposition modeling (FDM), and three dimensional printing (3DP) to precisely position bioactive agents(s) within a release matrix to control the rate of release and allow either a pulsed or constant release profile.

The macrostructure and porosity of the dosage forms of the '962 patent can be manipulated by controlling printing parameters, the type of polymer and particles size, as well as the solvent and/or binder. Porosity of the matrix walls, as well as the matrix per se, can be manipulated using SFF methods, especially 3DP. Structural elements that maintain the integrity of the devices during erosion can also be incorporated so that more linear release of incorporated material is obtained. Most importantly, these features can be designed and tailored using computer aided design (CAD) for individual patients to optimize drug therapy.

Despite the significant advances in drug delivery systems (DDS) described by U.S. Pat. No. 5,490,962, there is room for improvement implementing 3DP to produce suitable dosage forms. For example, the treatment of various disorders with multiple drug therapy may require different release rates for each drug. A single dosage form combining the multiple drugs would require separate domains for drug release at the different rates. Drugs having high potency and/or toxicity require special handling for both safety reasons and consistency in dose level. Other drugs may have low solubility in bodily fluids, requiring that they be modified for proper absorption. Certain drug therapies may require pulsatile release over prolonged periods.

The present invention addresses these needs.

SUMMARY OF THE INVENTION

It is accordingly an aspect of the invention to provide a multiphasic dosage form capable of providing delivery of multiple drugs having different release characteristics.

It is another aspect of the invention to provide a multiphasic dosage form, as above, which provides pulsatile release for one drug and continuous release for another drug.

It is yet another aspect of the invention to provide a multiphasic dosage form incorporating a small, precisely measured amount of a high potency and/or high toxicity drug.

It is yet another aspect of the invention to provide a multiphasic dosage form which provides adequate absorption of a drug which is sparingly soluble in bodily fluid.

It is another aspect of the invention to provide a method for making the above dosage forms.

These objects and others set forth more fully hereinbelow, are achieved by a method for forming a multiphasic dosage form containing one or more than one pharmaceutically active material. The method comprises the steps of (a) preparing a first layer of pharmaceutically acceptable particulates on a platform; (b) forming a first pattern of adhered particulates in the first layer by applying a binder to selected portions of the first layer, the first pattern incorporating one of the pharmaceutically active materials; (c) preparing a second layer of pharmaceutically acceptable particulates over the first layer; (d) forming a second pattern of adhered particulates which is the same or different from the first pattern, by applying a binder to selected portions of the second layer the second pattern incorporating a second pharmaceutically active material and being adhered to the first pattern along an interface thereof to thereby produce a three dimensional dosage form.

BRIEF DESCRIPTION OF THE DRAWINGS

For a full understanding of the invention, the following detailed description should be read in conjunction with the drawings, wherein.

DETAILED DESCRIPTION OF THE PREFERRED EMBODIMENTS

Solid free-form fabrication methods offer several unique opportunities for the construction of dosage forms. These dosage forms can be constructed with a specified drug composition gradient and structure so that the dosage regimes can be much more complex than currently practiced and tailored for the needs of individual patients. SFF methods can be used to selectively control composition within the build plane by varying the composition of printed material. This means that unconventional microstructures, such as those with complicated porous networks or unusual composition gradients, can be designed at a CAD terminal and built through an SFF process such as 3DP.

Three dimensional printing is described by Sachs, et al., "CAD-Casting: Direct Fabrication of Ceramic Shells and Cores by Three Dimensional Printing: Manufacturing Review 5 (2), 117–126 (1992) and U.S. Pat. No. 5,204,055, the teachings of which are incorporated herein. Suitable devices include both those with a continuous jet stream print head and a drop-on-demand (DOD) print head. A continuous jet head provides for a fluid that is pressure driven through a small orifice. Droplets naturally break off at a frequency that is a function of the fluids properties and the orifice diameter. Initial prototype dosage forms were built using a single jet head. Multiple jet heads are preferred.

A DOD printhead utilizes individual solenoid valves that run at frequencies up to 1.2 kHz. Fluid is also pressure driven through these valves and a small orifice is downstream of the valves to ensure accurate and repeatable droplet size.

Both raster and vector apparatuses can be used. When using DOD a raster apparatus provides that the printhead goes back and forth across the bed with the jet turning on and off. A continuous jet is always on, and a vector apparatus is used similar to an x-y printer. 3DP is used to create a solid object by ink-jet printing a binder onto selected areas of sequentially deposited layers of powder or particulates. In the following description, the terms "powder" and "particulates" are used interchangeably. Each layer is created by spreading a thin layer of powder over the surface of a powder bed. In a preferred embodiment, a moveable powder piston is located within a cylinder, with a powered roller to deliver dispensed powder to a receiving platform located adjacent to the powder feeder mechanism. Operation consists of raising the feed piston a predetermined amount for each increment of powder delivery. The roller then sweeps across the surface of the powder feeder cylinder and deposits it as a thin layer across the receiving platform immediately adjacent to the powder feeder. The powder feeding piston is then lowered as the roller is brought back to the home position, to prevent any back delivery of powder.

The powder piston and cylinder arrangement can also consist of multiple piston/cylinders located in a common housing, which would be used to dispense multiple powders in the following sequence:

1. Line up the first desired powder cylinder with the rolling/delivery mechanism
2. Increment the movable position piston up to deliver an incremental amount of powder
3. Activate roller to move powder to receiving platform
4. Lower the powder piston driving mechanism
5. Laterally slide the powder feeder housing such that the next desired powder cylinder is lined up with the delivery mechanism
6. Repeat steps 2, 3, 4 and 5
7. Continue for as many different powders and/or powder layers as required.

This method of powder feeding can be controlled manually or be fully automated. Cross contamination of different powders is minimized since each powder is contained in its own separate cylinder. One of the advantages to this method is that only one piston raising/lowering mechanism is required for operation, regardless of the number of powder cylinders. By raising the powder for delivery rather than dropping it from above, problems associated with gravity based delivery systems such as "ratholing", incomplete feed screw filling/emptying and "dusting" with the use of fine powders is eliminated or minimized since only enough energy is introduced to move the powder up an incremental amount. The powder feeder housing, with its multiple cylinders and pistons, can also be designed as a removable assembly, which would minimize changeover times from one powder system to another.

The powder bed is supported by a piston which descends upon powder spreading and printing of each layer (or, conversely, the ink jets and spreader are raised after printing of each layer and the bed remains stationary). Instructions for each layer are derived directly form a computer-aided design (CAD) representation of the component. The area to be printed is obtained by computing the area of intersection between the desired plane and the CAD representation of the object. The individual sliced segments or layers are jointed to form the three dimensional structure. The unbound powder supports temporarily unconnected portions of the component as the structure is built but is removed after completion of printing.

Figure 1:
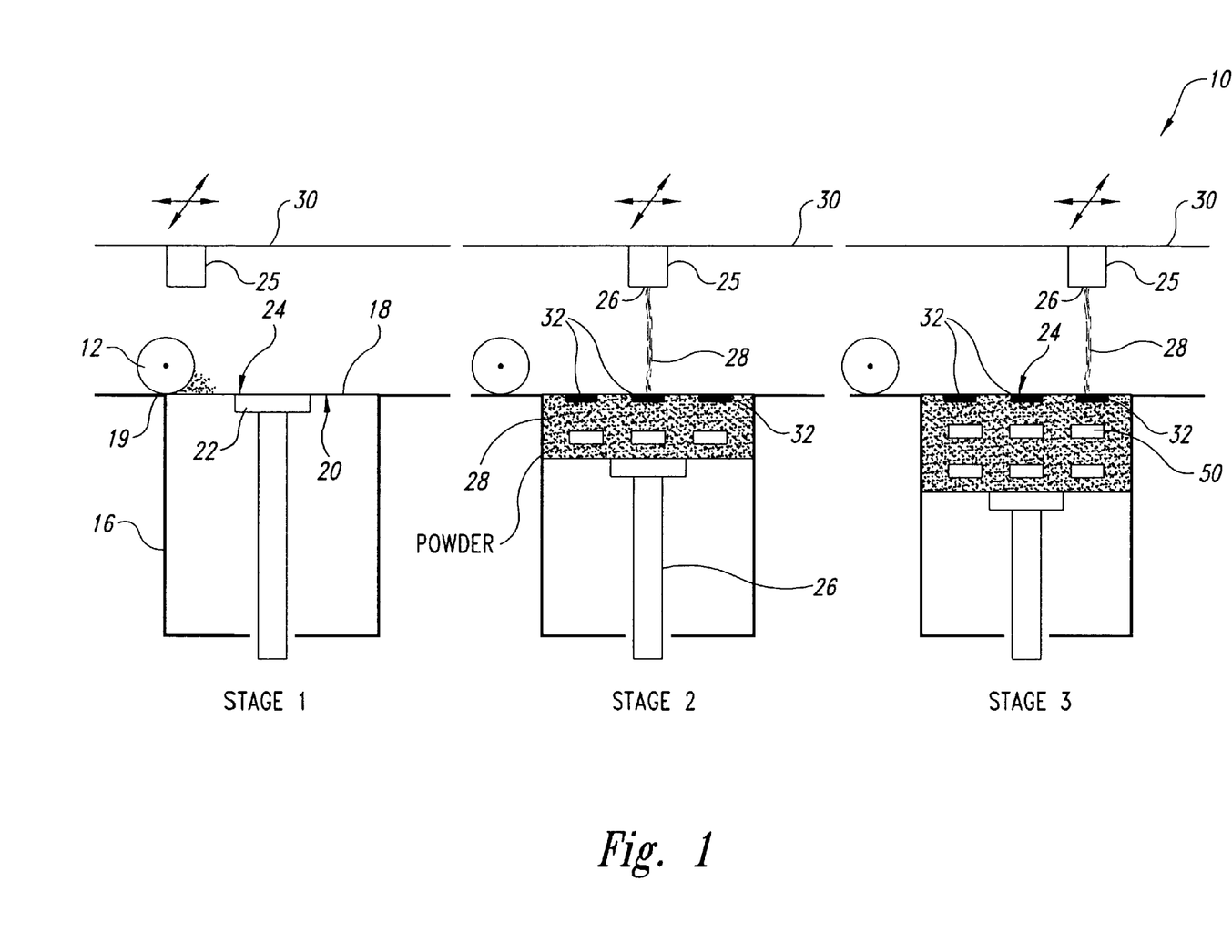
FIG. 1 is a schematic drawing of one embodiment of the process of the invention.

The 3DP process is shown schematically in FIG. 1, wherein a 3DP apparatus is indicated generally by the number 10. Powder 12 is rolled from a feeder source (not shown) in stage 1 with a powder spreader 14 onto a surface 16 of a build bed 18. The thickness of the spread layer is varied as a function of the type of dosage from being produced. Generally the thickness of the layer can vary from about 100 to about 200 $\mu$m. The printhead 22 then deposits the binder (fluid) 24 onto the powder layer and the build piston 26 is lowered one layer distance. Powder is again rolled onto the build bed 18 and the process is repeated until the dosage forms are completed (stages 2 and 3 of FIG. 1). The droplet size of the fluid is from about 50 to about 500 $\mu$m in diameter. Servo motors (not shown) are used to drive the various actions of the apparatus 10.

While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether or not further curing is required, the loose unbonded powder particles are removed using a suitable technique, such as ultrasonic cleaning, to leave a finished device.

As an alternative to ultrasonic cleaning, water soluble particulates may be used. Fabrication of structures with designed pore structures is a challenging task even with additive manufacturing processes such as 3DP. Cylindrical structures with radial pores of hundreds of microns in diameter can be fabricated, however, the removal of loose powder from the narrow channels requires a cumbersome manual clean up process. On solution is to employ mixtures of water soluble particulates (sodium chloride) with polymers used to fabricate specimens. The small particles then leach out to reveal an interconnected porous structure. While this technique is useful in fabricating a network of pores, control of pore architecture is lost. An improvement on this technique is to selectively deposit the soluble phase to form internal soluble patterns prior to building any external features. Water soluble materials such as poly(ethylene glycol) can be deposited on a flat surface prior to spreading a new layer of powder. This enables the process to build walls of soluble material. Loose powder can be spread after completion of the patterning. The external or insoluble features of the specimen can then be built by printing with binder solution. Following the requisite iterations of the patterning and printing processes, produces a dosage form that has intricate internal features that can be dissolved easily when immersed in an appropriate solvent. This concept can be used to fabricate components with controlled internal pore channels. These soluble patterns can also be used to create drug delivery devices with prescriptive release. Devices that are relatively insoluble in physiological fluids can be designed and fabricated with controlled soluble channels within. Upon ingestion or implantation, dissolution of the channels will expose the active that are isolated until the removal of the soluble phase in the channels.

Construction of a 3DP component can be viewed as the knitting together of structural elements that result from printing individual binder droplets into a powder bed. These elements are called microstructural primitives. The dimensions of the primitives determine the length scale over which the microstructure can be changed. Thus, the smallest region over which the concentration of bioactive agent can be varied has dimensions near that of individual droplet primitives. Droplet primitives have dimensions that are very similar to the width of line primitives formed by consecutive printing of droplets along a single line in the powder bed. The dimensions of the line primitive depend on the powder and the amount of binder printed per unit line length. A line primitive of 500 $\mu$m width is produced if an ink jet depositing 1.1 cc/min of methylene chloride is made to travel at 8"/sec over the surface of a polycaprolactone (PCL) powder bed with 45–75 $\mu$m particle size. Higher print head velocities and smaller particle size produce finer lines. The dimensions of the primitive seem to scale with that calculated on the assumption that the liquid binder or solvent needs to fill the pores of the region in the powder which forms the primitive.

Finer feature size is also achieved by printing polymer solutions rather than pure solvents. For example, a 10 wt. % PCL solution in chloroform produces 200 $\mu$m lines under the same conditions as above. The higher solution viscosity slows the migration of solvent away from the center of the primitive.

The solvent drying rate is an important variable in the production of polymer parts by 3DP. Very rapid drying of the solvent tends to cause warping of the printed component. Much, if not all, of the warping can be eliminated by choosing a solvent with a low vapor pressure. Thus, PCL parts prepared by printing chloroform have nearly undetectable amounts of warpage, while large parts made with methylene chloride exhibit significant warpage. It has been found that it is often convenient to combine solvents to achieve minimal warping and adequate bonding between the particles. Thus, an aggressive solvent can be mixed in small proportions with a solvent with lower vapor pressure.

There are two principal methods for incorporation of bioactive agent (e.g., a drug). In the first method, a layer of dispersed fine polymer powder is selectively bound by ink-jet printing a solvent onto the polymer particles which dissolves the polymer. This process is repeated for subsequent layers to build up the cylinder, printing directly on top of the preceding layer, until the desired shape is achieved. If it is desired to design a constant rate release matrix, the drug is dissolved or dispersed (e.g., micellar) in the solvent, yielding drug dispersed evenly through the matrix. The printing process for this case would then be continued layer by layer until the desired shape was obtained.

In the second method, devices for pulsed release of drugs are prepared by constructing drug-rich regions within the polymer matrix. In this case, multiple printheads are used to deposit drug containing solvent in selected regions of the powder bed. The remaining volume of the desired device is bound with pure solvent deposited by a separate printhead. The printing process is repeated layer by layer to yield a device which gives a pulsed release of drug. For example, a cylindrical device could contain a cylindrical annulus region which is enriched with a drug.

Significant amounts of matter can be deposited in selected regions of a component on a 100 $\mu$m scale by printing solid dispersions or solid precursors through the ink-jet print heads with hundreds of jets can be incorporated into the process. The large number of individually controlled jets make high rate 3DP construction possible.

A specific embodiment of the invention, the dosage form can incorporate a solubility or stability enhancer. Suitable materials in this regard are cyclodextrins, cyclodextrin derivatives and/or substances that spontaneously form micelles as solubility/stability enhancers to facilitate the dispensing procedure, as well as the releasing pattern of poorly/sparingly soluble or unstable drugs in the fabrication of 3DP drug delivery systems (i.e. tablets, implants, etc.). Cyclodextrins (CDs) and their derivatives are commonly used complexing agents (CA). When incorporated in the fabrication of 3DP dosage forms, CDs can be used as follows:

1. to prepare aqueous solutions of sparingly soluble drugs so they can be dispensed in sufficient concentration through the nozzle, thus avoiding the use of suspensions and minimizing the need for extensive solvent removal or drying,
2. to increase drug stability by preventing labile groups/molecules from interacting with solvent,
3. to form a drug complex in situ, so that wetting and solublilzation are enhanced when in contact with GIT fluids (oral DDS) or subcutaneous fluids (implantable DDS). This substantially improves the rate of delivery leading to a desirable fast onset of therapeutic activity, and,
4. as a corollary of 3 above, when CA is placed at the bottom of a reservoir (designed within the dosage form) it will act as a carrier that facilitates/assists the release of remaining drug, which in turn leads to the desired fast offset of activity and prevents undesirable leaching out of sub-therapeutic drug levels.

By properly combining 3 and 4 above, a desirable pulsing pattern can be achieved.

By combining the properties of drug-complex systems with the 3DP fabrication process the three scenarios and any combination/variation of them can be produced/modeled to provide a solution to a particular drug release profile to be achieved.

Surface finish of the dosage forms of the invention is governed by the physical characteristics of the materials used as well as the build parameters. These factors include particle size, powder packing, surface characteristics of the particles and printed binder (i.e. contact angle), exit velocity of the binder jet, binder saturation, layer height, and line spacing. Interaction of the binder liquid with the powder surface, in particular, can be controlled carefully to minimize surface roughness. In a case where the binder gets wicked out in a large area, the feature size control becomes difficult, resulting in a rough surface.

In one embodiment, the invention circumvents this problem in cases where no substitute material combinations can be found. An intermediary material can be deposited on a powder bed to form a wetting barrier for the binder material. These intermediaries are deposited in such as fashion that spreading of the subsequently printed binder is hindered by the presence of the "outlining" intermediary region. An extreme example will be the printing of an oil around the specimen to limit wicking of a water-based binder.

A number of materials are commonly used to form a matrix for bioactive agent delivery. Unless otherwise specified, the term "polymer" will be used to include any of the materials used to form the bioactive agent matrix, including polymers and monomers which can be polymerized or adhered to form an integral unit. In a preferred embodiment the particles are formed of a polymer, such as a synthetic thermoplastic polymer, for example, ethylene vinyl acetate, poly(anhydrides), polyorthoesters, polymers of lactic acid and glycolic acid and other α hydroxy acids, and polyphosphazenes, a protein polymer, for example, albumin or collagen, or a polysaccharide containing sugar units such as lactose. The polymer can be non-biodegradable or biodegradable, typically via hydrolysis or enzymatic cleavage. Non-polymeric materials can also be used to form the matrix and are included within the term "polymer" unless otherwise specified. Examples include organic and inorganic materials such as hydoxyapatite, calcium carbonate, buffering agents, and lactose, as well as other common excipients used in drugs, which are solidified by application of adhesive rather than solvent.

Erodible bioactive agent delivery devices are one of the simplest medical devices that can be constructed. These types of bioactive agent delivery devices can be used in an oral or implantable form depending on the desired method for delivering the specific bioactive agent. They differ in the time period over which the bioactive agent is delivered and excipients used in the device construction. Erodible bioactive agent delivery systems are constructed by dispersing the desired bioactive agent in a matrix chosen so that it dissolves or decomposes in the presence of a body fluid. Oral erodible systems, for example, begin to dissolve when they contact with body fluid. In principle, release of the bioactive agent in both cases is controlled both by the rate at which the excipient reacts with the fluid and the rate of bioactive agent diffusion out of the device. This is true only if the surface of the device erodes in a uniform manner and its internal structure remains unchanged by prior reaction at the surface.

Photopolymerizable, biocompatible water-soluble polymers include polyethylene glycol tetraacrylate (MW 18,500) which can be photopolymerized with an argon laser under biologically compatible conditions using an imitator such as triethanolamine, N-vinylpyrollidone, and eosin Y. Similar photopolymerizable macromers having a poly(ethylene glycol) central block, extended with hydrolyzable oligomers such as oligo(d,1-lactic acid) or oligo (glycolic acid) and terminated with acrylate groups, may be used.

Examples of biocompatible polymers with low melting temperatures include polyethyleneglycol 400 which melts at 4°–8° C., PEG 600 melts at 20°–25° C., and PEG 1500 which melts at 44°–48° C., and stearic acid which melts at 70° C. Other suitable polymers can be obtained by reference to The Polymer Handbook, $3^{rd}$ edition (Wiley, N.Y. 1989), the teachings of which are incorporated herein. The material for construction of the devices is selected based on the mechanism of drug transport and compatibility of their processing technology with the stability of the bioactive agent.

The binder can be a solvent for the polymer and/or bioactive agent or an adhesive which binds the polymer particles. Solvents for most of the thermoplastic polymers are known, for example, methylene chloride or other organic solvents. Organic and aqueous solvents for the protein and polysaccharide polymers are also known, although an aqueous solution is preferred if denaturation of the protein is to be avoided. In some cases, however, binding is best achieved by denaturation of the protein.

The binder can be the same material as is used in conventional powder processing methods or may be designed to ultimately yield the same binder through chemical or physical changes that take place in the powder bed after printing, for example, as a result of heating, photopolymerization, or catalysis.

The selection of the solvent for the bioactive agent depends on the desired mode of release. In the case of an erodible device, the solvent is selected to either dissolve the matrix or is selected to contain a second polymer which is deposited along with the drug. In the first case. the printed droplet locally dissolves the polymer powder and begins to evaporate. The drug is effectively deposited in the polymer powder after evaporation since the dissolved polymer is deposited along with the drug. The case where both the drug and a polymer are dissolved in the printed solution is useful in cases where the powder layer is not soluble in the solvent. In this case, binding is achieved by deposition of the drug polymer composite at the necks between the powder particles so that they are effectively bound together.

Aggressive solvents tend to nearly dissolve the particles and reprecipitate dense polymer upon drying. The time for drying is primarily determined by the vapor pressure of the solvent. There is a range from one extreme over which the polymer is very soluble, for example, 30 weight percent solubility, which allows the polymer to dissolve very quickly, during the time required to print one layer, as compared with lower solubilities. The degree to which the particles are attacked depends on the particle size and the solubility of the polymer in the solvent. Fine powder is more completely dissolved than powder with larger particles size.

There are essentially no limitations on the bioactive agents that can be incorporated into the devices, although those materials which can be processed into particles using spray drying, atomization, grinding, or other standard methodology, or those materials which can be formed into emulsifications, microparticles, liposomes, or other small particles, and which remain stable chemically and retain biological activity in a polymeric matrix, are preferred. Those bioactive agents which can be directly dissolved in a biocompatible solvent are highly preferred. Bioactive agents also include compounds having principally a structural role, for example, hydroxyapatite crystals in a matrix for bone regeneration. The particles may have a size of greater than or less than the particle size or the polymer particles used to make the matrix.

Examples generally include proteins and peptides, polysaccharides, nucleic acids, lipids, and non-protein organic and inorganic compounds, referred to herein as "bioactive agents" unless specifically state otherwise. These materials have biological effects including, but not limited to anti-inflammatories, antimicrobials, anti-cancer, antivirals, hormones, antioxidants, channel blockers, growth factor, cytokines, lymphokines, and vaccines. It is also possible to incorporate materials not exerting a biological effect such as air, radiopaque materials such as barium, or other imaging agents.

EXAMPLE 1
Intraocular Device Capable of Delivering an Anti-inflammatory and Antiproliferative Drug Anti-proliferative and anti-inflammatory agents are used to treat a number of ocular diseases, including traction retinal detachment, that often result in blindness. Traction retinal detachment can develop in proliferative retinal diseases, such as proliferative diabetic retinopathy or after penetrating ocular trauma. The anti-proliferative, 5-fluorouracil (5-FU), and the anti-inflammatory, diclofenac, are used to construct dosage forms using 3DP with the objective to contemporaneously deliver 5-FU in a pulsatile manner and diclofenac at a constant rate from the same device. The dosage form has its application in the treatment of the proliferation and inflammation resulting from traction retinal detachment, especially after trauma. Anit-proliferatives like 5-FU can be extremely toxic; in such cases, pulsed intraocular delivery could produce the same therapeutic benefits as continuous release while reducing side effects, toxicity in normal cells, and the risk of multiple drug resistance (MDR) in fibrous cells, thereby enhancing the efficacy of the treatment. Diclofenac, on the other hand, is less toxic and is effective when delivered at a constant rate.

The first step of the procedure is to optimize prescriptive release rates of 5-FU and diclofenac independently and thereafter combine the two substructures into one device. The latter process is accomplished by 3DP fabrication during a single manufacturing process.

Methods and Results

The implant that can be divided into two portions. The top portion consists of the 5-FU chambers and the lid layers that encapsulate the actives. These caps are designed to degrade at different rates to cause the drug to release at predetermined lag times. The lower portion of the implant releases diclofenac at zero-order kinetics throughout the therapy. Different portions of the intravitreal implant mandate distinct characteristics that cannot be achieved from a monolithic structure. Internal structure and composition at each portion of the implant device are controlled individually to meet the release characteristics criteria.

Polymeric film degradation experiments are conducted to quickly identify candidate materials for constructing the intraocular implant devices. The initial polymer selection is limited to products that are approved by the United States FDA for use in humans. in addition, some of these polymers such as polyanhydrides are not widely available commercially. The polymers tested are further limited to those commercially available and those that could be prepared in powder form, however, other products may have characteristics which are suitable in some but not all of these criteria and are included within the scope of the present invention.

Different copolymers of the polyactides and polyglycolides of a wide range of molecular weights are studied. These include polylactide-co-glycolide (PLGA) with varying lactide: glycolide ratio (75:25, 50:50) and molecular weights ranging from 15 KDa to 60 KDa. Among the low molecular weight polyactides tested are poly (l-lactide) 2 KDa. A number of different polyanhydrides are also evaluated for fast eroding lids. These include polysebacic acid (PSA), polyfatty acid dimer-sebacic acid (PFAD:SA; 50:50, 51 KDa), polyricinoleic acid maleate-sebacic acid (PRAM:SA, 50:50, 34 KDa).

PLGA is chosen to form the slow eroding walls of the implant based on the film degradation study. Polyanhydrides, especially P(FAD:SA) exhibit fast erosion characteristics. This makes P(FAD:SA) an ideal system to be used in construction of the 5-FU caps. The surface erosion mechanism of polyanhydrides also suggests that different thickness films can be used to control the lag time.

Pulsatile Release Implants

A number of prototype intraocular implant devices are fabricated by 3DP. One implant has four chambers containing 5-FU. Walls of the implant are fabricated by printing chloroform into thinly spread PLGA powders. Only the printed region became dense while the PLGA powder from the unprinted region remains unbound. A scanning electron micrograph (SEM) taken from the center of the device is used to confirm that the microstructures desired, formation of four distinct compartments, during 3DP fabrication process are achieved.

Two orthogonal walls form the separation between the four chambers of the implant devices fabricated. Two different devices are constructed by printing 8 lines side by side in one and 4 lines side by side in the other. Visible evidence from scanning electron micrographs demonstrates that the resulting wall thickness increases as the number of printing lines increases. Differences in the release characteristics from these implant devices are also a function of printing line number and therefore wall thickness.

Prototype implant devices are manually loaded with 160 µg 5-FU and polymeric caps are constructed on top of the chambers to encapsulate the active agent. P(FAD:SA) powders are used to build caps of different thicknesses. The PLGA walls are saturated with chloroform to enhance bonding to the P(FAD:SA) layer. Prototype implant devices that are fabricated with the presaturation steps do not exhibit any immediate dose dumping. Another design feature implemented to avoid premature dumping of 5FU is an increase in the side wall thickness. This feature served a dual purpose. The increased wall thickness effectively decreases the chance of 5-FU permeation through the side walls. At the same time, the contact surface area between the side walls of the chamber and the top lid is increased, thus minimizing 5-FU release from the PLGA and P(FAD:SA) interface.

Drug release is analyzed by immersing the dosage in 10 ml of phosphate buffered saline (PBS) solution kept at 37° C. Samples are taken at predetermined intervals (at least 5 per assay) and analyzed using quantitative HPLC. Approximately 90% of the drug is released, approximately 146 µg in separate bursts. A number of different prototype implant device designs are tested and yield distinctively different release characteristics.

The release profile from four sets of different prototype designs are measured using an HPLC method. The first profile labeled as Prototype 3 is taken from implant devices with porous and loosely attached P(FAD:SA) lid layers. These implants showed complete 5-FU release within the first 24 hours of the study. This demonstrates that the 5-FU in the implant devices will pulse out rapidly from the microchambers when there are enough pores to allow channeling of the release medium. Modifications made in the processing conditions for Prototype 4 result in pore-free lid layers as was discussed earlier. The release profile of Prototype 4 shows a significant difference from that of Prototype 3. A short lag time of ~6 hours with peak release at 14 hours is observed with Prototype 4 devices. These implant devices exhibit imperfections at the PLGA and P(FAD:SA) interface to which could be attributed the relatively quick release of 5-FU. Further improvements in the fabrication sequence and increased side all thickness resulted in improved bonding between the PLGA walls and the P(FAD:SA) lid layers. Release profiles of Prototype 5 clearly demonstrated lag times of 24 hours or 36 hours, depending on the number of lid layers. The number of P(FAD:SA) lid layers also affect the release rates. A peak release rate of 5 µg per hour is achieved at 43 hours for the implants with 2 lid layers while implants with 3 lid layers reach a peak of 2.5 µg per hour in 56 hours.

These data demonstrate that modifications in process parameters and implant design may be used to achieve pulsatile release of drugs from implants. Close examination of the pulses form the prototype implants suggest that once the implant configuration and material system is optimized, multiple pulses from a single implant may be achieved.

In addition to the material systems investigated, other material systems that would erode faster without allowing significant diffusion can be used for achieving pulsatile release. A further embodiment of the present invention is a device in which the device design is modified in order to allow sequential exposure of the lid layers. In the proposed configuration, sequential inner 5-FU chambers are exposed to the release medium and only the contents from the first chamber are exhausted.

Continuous Release Implants

Before fabrication of implant devices can be achieved, the optimal 3DP parameters are determined. Polyesters are used as the polymer phase, which are soluble in chloroform. Diclofenac is insoluble in chloroform but readily soluble in methanol. The solubility of diclofenac in different ratios of methanol and chloroform is investigated in order to optimize the balance of high drug concentration and polymer dissolution ability of the binder solution. In addition, the ability of these solvent combinations to dissolve polyesters is examined. It is determined that a 20:80 mixture of methanol:chloroform is optimal for dissolving the polymer while delivering a high concentration of drug to the device. A homogeneous implant is achieved by incorporating 24 mg/ml of diclofenac into the binder solution, which is deposited on a bed of polyester polymer.

Several diclofenac-containing prototypes are successfully fabricated using the 3DP technology and tested for drug release in static phosphate buffered saline solution at 37° C. An HPLC assay is developed and tested for linearity, precision, specificity, and sensitivity prior to quantitative analysis of diclofenac.

a. Diclofenac prototype 1

Six disks from the first prototype batch are exposed to liquid $CO_2$, to remove residual chloroform and determine if this process affects the diclofenac content. However, the amount of diclofenac in the disks exposed to liquid $CO_2$ is 7.2±0.2 mg (n=3), which is the same as disks not subjected to liquid $CO_2$. The amount of residual chloroform in disks exposed to liquid $CO_2$ is 1.9±0.3% (n=3), compared to 5.5±0.3% (n=3) for control devices not exposed to liquid CO2. Thus, exposure to liquid CO2 under these conditions reduces the amount of chloroform by 65% but does not affect diclofenac content.

These disks are homogenous with diclofenac distributed throughout the entire disk. The actual implant will contain an additional portion for the pulsatile release of separate drug (i.e., 5-FU), thus, only one major face of the diclofenac section will be directly exposed to the external environment. As a result, subsequent prototypes contain a placebo section to mimic the pulsatile section of the final implant device.

b. Diclofenac, prototype 2

Initial prototypes of the diclofenac intravitreal implant exhibit high rate of release for 2 days (0.8 and 0.6 mg per day on days 1 and 2, respectively) which is attributable to the large, drug containing surface area of the implant exposed to the dissolution medium. Thereafter, diclofenac release is continuous at measurable but sub-therapeutic rates (greater than 0.08 but less than 0.36 mg per day) for an additional 14 days.

c. Diclofenac prototype 3

The second generation of prototypes is fabricated with a large fraction of the diclofenac-containing component capped with placebo polymer layers of different thickness. This results in a initial drug release that tapers and then gradually exceeds the target rate of 80 ug per day after 10 days. Furthermore, complete drug release was not observed within the desired sixteen days.

d. Diclofenac prototype 4

This batch is similar to Prototype 3 except that the placebo cap is fabricated with 30% sodium chloride to create holes in the cap to increase the initial release of diclofenac. This technique increases diclofenac release during the first day, but for the next 13 days, the release rate is low, similar to prototype 3.

e. Diclofenac prototype 5

The previous prototypes exhibit drug release rates that vary from high to low release or low to high release. To achieve zero-order release, the interconnectivity of the diclofenac particles in the polymer phase is increased without altering the drug loading by using sodium chloride as an inert filler. Thus, prototype 5 disks are fabricated with a blend of PLGA polymer with sodium chloride. The addition of 35% (w/w) sodium chloride ensures that the combined loading of diclofenac and sodium chloride is above the minimum necessary to create interconnected particles. A void volume or drug occupancy of 35% is recognized as above the minimum necessary to establish complete interconnection of all pores and channels within a porous structure and is well known by those skilled in the art as "percolation theory." These prototypes are also covered with a placebo polymer coating to inhibit initial dose dumping by the implant. The results of this study indicate that Prototype 5b exhibits the target diclofenac release rage of 80 µg/day.

f. Solvent Extraction

Preliminary experiments on post-fabrication exposure of the diclofenac prototypes to liquid CO2 for 5, 30, and 60 minutes indicate that the procedure reduces the amount of residual solvent in the implant devices without significantly affecting diclofenac content. The results are summarized in Table 1.

TABLE 1

Effect of liquid CO2 exposure time on diclofenac content in devices manufactured by 3DP using polylactide-co-glycolide as the polymer and chloroform as the binder.

| Prototype # | $CO_2$ Exposure (min) | Diclofenac (mg) | Control Diclofenac (mg) | Residual Chloroform (wt %) |
| --- | --- | --- | --- | --- |
| 1 | 5 | 7.30 | 7.3 ± 0.2 | 2.19 |
| 1 | 5 | 7.36 | 7.3 ± 0.2 | 1.67 |
| 1 | 5 | 7.07 | 7.3 ± 0.2 | 1.83 |
| 3 | 30 | 1.014 | 1.23 ± 0.02 | 0.35 |
| 3 | 60 | 1.038 | 1.23 ± 0.02 | 0.39 |
| 3 | 60 | 1.007 | 1.23 ± 0.02 | 0.17 |
| 4 | 30 | 0.994 | 1.02 ± 0.09 | 0.12 |
| 4 | 60 | 0.995 | 1.02 ± 0.09 | 0.18 |

These results demonstrate that the fabrication of a implantable device or oral dosing device using 3DP can be manipulated to produce a single device exhibiting both pulsatile and continuous active release over periods as long as days or weeks.

EXAMPLE 2
Contraceptive Implant Containing 17-DAN

A contraceptive implant device was designed for cyclic release of 17-diacetylnorgestimate (17-DAN). Biodegradable polyesters of different types and molecular weights including poly-l-lactic acid (PLLA) and poly-epsilon-caprolactone (PCL) are used to construct different regions of prototype devices in a single contiguous process. The regions formed included a slow-degrading outer framework as a drug release restraint, a drug-carrying core, and a diffusion layer for drug delivery rate control. The drug is incorporated in the implant core surrounded by three impermeable walls and one permeable wall. The printing parameters are also optimized to minimize the presence of defects.

A device that in final dimension is 1.5 cm×1.5 cm×3.5 cm and containing 200 $\mu$g of 17-DAN in a central core is fabricated. The releasing layer is composed of either PCL or PLLA printed with 20% of low molecular weight PCL/chloroform. The non-releasing layer is composed of PLLA printed with 2.5% PCL/chloroform.

In one of the experiments, the permeable wall is replaced by an impermeable wall. The implant shows no drug release, clearly demonstrating the ability to fabricate biodegradable surfaces that are impervious.

EXAMPLE 3

Fabrication of microdose oral dosage forms by conventional tablet pressing technique presents many content uniformity issues and safety hazards. 3DP processing can be used to build highly accurate dosage forms by depositing metered amounts of medicaments(s) in the center portion of the dosage form. Since the medicament can be completely encapsulated therein, the content uniformity will not be altered by subsequent handling, packaging, or during storage. Furthermore, it will be recognized that the safety hazards due to exposure to the medicament being used to persons involved in the manufacture o the dosage forms are immediately reduced. The framework for micro-dosage tablets built by 3DP further allows the release rate of the medicament from the center portion to be controlled by the methods described herein and as previously set forth in U.S. Pat. No. 5,490,962.

In one particularly preferred embodiment, an oral dosage form of the present invention is constructed to release hormones in submilligram quantities. The combination of norethindrone acetate and ethinyl estradiol is one such combination contemplated. The active component may be 500 $\mu$g of norethindrone acetate and 2.5 $\mu$g of ethinyl estradiol. The powder material used may be selected from microcrystalline cellulose, lactose, arabinogalctans, starch, or super disintegrant. The binder solution composition may contain arbinogalactans or Eudragits (e.g. a methacrylate). The architecture of the dosage form may be of single chamber type or include multiple active chambers in order to effect the desired release profile of both agents from the dosage form.

EXAMPLE 4
Materials

Sure-Jell® (Kraft General Foods, Inc., White Plains, N.Y., Lot 6-032-P-0659-4, exp. February 1999) powder is used to build the framework for the microdose tablets (dosage forms). Fruit pectin is the major ingredient of Sure-Jell. Fumaric acid is also present to assist gelling of the powder. As-received powder is fractionated by sieving through 100 mesh and 325 mesh screens to remove large agglomerates and fines. The tablets are built by using only the powder that is left on the 325 mesh screen (d+45~150 $\mu$m). Deionized water is used to bind the Sure-Jell powder.

The active ingredient used in this set of microdose tablets is an antibacterial drug called nitrofurantoin (Sigma Specialty Chemicals, St. Louis, Mo., Lot 115H1012). An ethanolic (Aldrich, Milwaukee, Wis., Lot 15013 HQ) solution of nitrofurantoin is deposited. The concentration of the solution is 0.0188 mg/ml.

Fabrication

The 3DP parameters used to build the framework for microdosage forms are explained below. Sure-Jell powder is spread into 170 $\mu$m layers by manual spreading, using a stainless steel rod. The flow rate of the binder, distilled water, is kept at 1.2 cc/min. Speed of the fast axis is 1.5 m/sec and each line is separated by 170 $\mu$m from the others. A spring steel stencil (Rache Corp., Camarillo, Calif.) with an 11×11 array of 1.04 cm circular openings is used to define the shape of the dosage forms. Ten 170 $\mu$m base layers are built with Sure-Jell and water and active solution is deposited on the top surface of the tenth layer.

The flow rate of the nitrofurantoin solution is kept at 1.0 cc/min and raster speed is kept at 1.6 m/sec. The active solution is dispensed throughout the entire surface of the tenth layer to achieve the dosage level of 1 $\mu$g per tablet. Total 5.32 $\mu$L of nitrofurantoin solution is delivered per tablet. These parameters were calculated based on the line spacing of 170 $\mu$m and the estimated total line segment of 51.02 cm to cover the circular surface area of each dosage form.

After drying the active solution by waiting for 60 minutes, another 170 $\mu$m layer of Sure-Jell is spread on the top of the dosage forms and bound to the drug containing layer with distilled water. This top layer is designed to cover the active-containing region and prevent the loss of active ingredient during handling processes.

The tablets are allowed to air dry for 30 minutes, then the powder bed is removed from TheriForm Alpha-0 machine and kept under vacuum (−760 mmHg) for 30 minutes to facilitate the removal of residual moisture. Each dosage form is removed from the powder bed manually.

Analytical Methods

An ethanol extraction method is used to prepare the assay samples for UV-analysis (BioSpec1601, Shimadzu, Princeton, N.J.). Each tablet is ground to powder form using an agate mortar and pestle. Caution is taken not to lose parts of the dosage form during the grinding process. The ground powder form of the tablet is transferred into vials. Five ml aliquots of ethanol are added to each vial using micro-pipettes (Eppendorf, Brinkmann Instruments, Westbury, N.Y.) and mixed for 15 minutes on an orbital shaker (Environ Shaker, Lab-Line Instruments, Melrose Park, Ill.). Ethanol dissolves only two major ingredients of the dosage form: nitrofurantoin and fumaric acid. Nylon Acrodiscs (Gelman Sciences, Ann Arbor, Mich.) were used to filter out particulates from the samples in order to minimize interference. UV-maximum for nitrofurantoin is at 356 nm while that of fumaric acid is around 270 nm. The UV-absorbance at 356 nm was taken to estimate the amount of nitrofurantoin in each of the sample dosage forms. The assay concentration of nitrofurantoin was in a well defined linear response region. A total of 18 tablets were tested for content uniformity.

Results

The UV-absorbance and corresponding nitrofurantoin content per individual dosage form is summarized in Table 1.

TABLE 1

Content Uniformity of Nitrofurantoin Microdosage Forms

| Sample ID | UV-absorbance | Nitrofurantoin per tablet ($\mu$g) |
|---|---|---|
| 1 | 0.0112 | 0.936 |
| 2 | 0.0139 | 1.160 |
| 3 | 0.0142 | 1.190 |
| 4 | 0.0118 | 0.987 |
| 5 | 0.0129 | 1.078 |
| 6 | 0.0106 | 0.883 |
| 7 | 0.0131 | 1.099 |
| 8 | 0.0105 | 0.875 |
| 9 | 0.0096 | 0.804 |
| 10 | 0.0114 | 0.956 |
| 11 | 0.0111 | 0.926 |
| 12 | 0.0129 | 1.078 |
| 13 | 0.0118 | 0.987 |
| 14 | 0.0117 | 0.977 |
| 15 | 0.0140 | 1.170 |
| 16 | 0.0118 | 0.987 |
| 17 | 0.0120 | 1.007 |
| 18 | 0.0140 | 1.170 |

The lowest dose is 0.804 $\mu$g while the highest was 1.190 $\mu$g. Average of the 18 specimens was 1.01 $\mu$g per tablet with a standard deviation of 0.113 $\mu$g (RSD=11.13%).

Figure 2A:
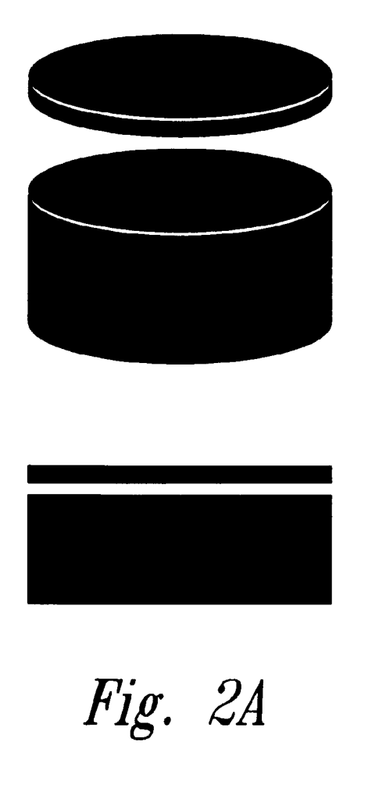
FIG. 2(a) is one embodiment of a microdose dosage form of the invention.
Figure 2B:
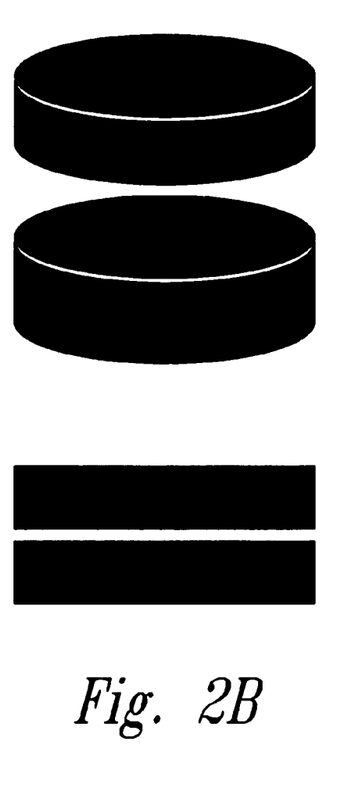
FIG. 2(b) is another embodiment of a microdose dosage form.
Figure 2C:
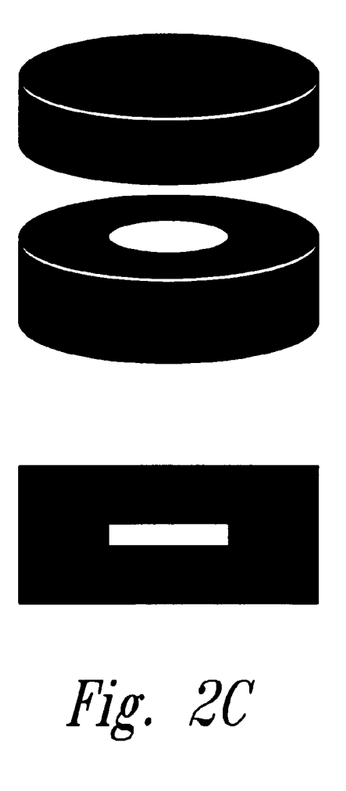
FIG. 2(c) is a dosage form of the invention showing total encapsulation.

The above procedure demonstrates the ability to build dosage forms with very small amount of drug. Average content of 1.015 $\mu$g is only 1% off from the intended dose. USP requirements for content uniformity mandates that dosage units fall within the range of 85% to 115% and the RSD less than or equal to 6.0%. The variability between dosage forms can be reduced by fine tuning the process. FIG. 2(a) illustrate one embodiment which may be susceptible to edge losses. Minor modifications can be made to the tablet design so that the active-containing region is less prone to edge losses during handling as shown in FIG. 2(b). An even more robust and safer architecture will encapsulate the active completely as shown in FIG. 2(c). This architecture has an advantage of eliminating the danger of exposing the highly potent pharmaceutical agents to the hands of the workers and patients, container walls, and neighboring tablets.

What is claimed is:

1. A multiphasic dosage form comprising a three dimensional matrix including pharmaceutically acceptable particulates adhered together;
   at least one pharmaceutically active material incorporated into the matrix; and
   at least one complexing agent incorporated into the matrix and in contact with the pharmaceutically active material.

2. A multiphasic dosage form as claimed in claim 1, wherein the complexing agent comprises a substance that forms micelles.

3. A multiphasic dosage form comprising a three dimensional matrix including pharmaceutically acceptable particulates adhered together; at least one pharmaceutically active material incorporated into the matrix; and at least one complexing agent incorporated into the matrix and in contact with the pharmaceutically active material wherein the complexing agent comprises a cylcodextrin or a derivative thereof.

4. A non-compressed drug delivery system comprising one or more active ingredients and a solid matrix harboring said one or more active ingredients, said matrix having a three dimensional architecture suitable for administration to a subject and which matrix comprises a bulk material and a binder, and which binder causes adhesion between the bulk materials and the binder, said bulk material being a biocompatible compound in a powder form and said binder comprising a pharmaceutically acceptable substance that together with said bulk material permits said matrix to maintain its three-dimensional architecture such that said pharmaceutical composition is released in a multiphasic pattern and said composition exhibits hardness and friability characteristics adequate to permit storage and handling of said composition.

5. A drug delivery system as claimed in claim 4, wherein the drug delivery system comprises at least two active ingredients and wherein the second active ingredient is released in a continuous pattern.

6. A drug delivery system as claimed in claim 4, wherein the drug delivery system comprises at least two active ingredients and wherein the second active ingredient is released in a multiphasic pattern.

7. A drug delivery system as claimed in claim 4, wherein the drug delivery system is an oral dosage form comprising a pill, tablet, or capsule.

8. A drug delivery system as claimed in claim 4, wherein the drug delivery system comprises a tissue scaffold, an implantable device or a patch.

9. A drug delivery system as claimed in claim 4, wherein the active ingredient is present in sub-milligram quantities.

10. A drug delivery system as claimed in claim 9, wherein the active ingredient comprises a natural or synthetic hormone, growth factor, a cytokine or a lymphokine.

11. A drug delivery system as claimed in claim 9, wherein the active ingredient is present in an amount of less than about 100 $\mu$g.

12. A drug delivery system as claimed in claim 4, wherein the content uniformity of the active ingredient is controlled within a factor of no more than 15% between systems.

13. A drug delivery system as claimed in claim 4, wherein the content uniformity of the active ingredient is controlled within a factor of no more than 5% between systems.

14. A drug delivery system as claimed in claim 4, wherein the release of the active ingredient is accurately controlled.

15. The multiphasic dosage form of claim 1 further including, at least one of the pharmaceutically active material on the complexing agent having a non linear concentration gradient along an axis of the dosage form.

* * * * *